US009492331B2

(12) United States Patent
Uematsu et al.

(10) Patent No.: US 9,492,331 B2
(45) Date of Patent: Nov. 15, 2016

(54) ABSORBENT ARTICLE WITH COMPRESSED GROOVES

(75) Inventors: Katsuhiro Uematsu, Kagawa (JP); Quing Cao, Shanghai (CN); Yukihiro Ito, Kagawa (JP); Hiroyuki Harada, Kagawa (JP); Kazuya Nishitani, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 153 days.

(21) Appl. No.: 13/818,818

(22) PCT Filed: Aug. 30, 2011

(86) PCT No.: PCT/JP2011/069604
§ 371 (c)(1),
(2), (4) Date: Jun. 11, 2013

(87) PCT Pub. No.: WO2012/029777
PCT Pub. Date: Mar. 8, 2012

(65) Prior Publication Data
US 2013/0267926 A1    Oct. 10, 2013

(30) Foreign Application Priority Data

Sep. 1, 2010 (JP) .................. 2010-195861

(51) Int. Cl.
*A61F 13/15*    (2006.01)
*A61F 13/20*    (2006.01)
*A61F 13/475*   (2006.01)

(52) U.S. Cl.
CPC ....... *A61F 13/4758* (2013.01); *A61F 13/4756* (2013.01)

(58) Field of Classification Search
USPC ............... 604/378–380, 385.01, 385.101
See application file for complete search history.

(56) References Cited

U.S. PATENT DOCUMENTS

| 5,674,341 A | 10/1997 | Ng |
| 5,795,345 A | 8/1998 | Mizutani et al. |
| 2004/0127875 A1 | 7/2004 | Hammons et al. |

(Continued)

FOREIGN PATENT DOCUMENTS

| CN | 202086678 U | 12/2011 |
| EP | 0249405 A2 | 12/1987 |

(Continued)

OTHER PUBLICATIONS

Extended European Search Report issued Jun. 18, 2014, corresponds to European patent application No. 11821793.4.

(Continued)

*Primary Examiner* — Michele M Kidwell
(74) *Attorney, Agent, or Firm* — Hauptman Ham, LLP

(57) ABSTRACT

To provide an absorbent article that can further reduce leakage of body fluid from an end portion in a longitudinal direction. An elongated shaped absorbent article includes: a top sheet that has a skin contacting surface; a back sheet; and an absorbent core that is disposed between the top sheet and the back sheet, in which a compressed groove is formed on the skin contacting surface; the skin contacting surface has an excretory contact region, a front region, and a rear region; the compressed groove has a pair of first central grooves and a first circular groove that is provided in at least any one of the front region and the rear region; and the first circular groove is arranged at a position overlapping a vertical center line.

10 Claims, 6 Drawing Sheets

(56) References Cited

U.S. PATENT DOCUMENTS

| | | |
|---|---|---|
| 2007/0073253 A1 | 3/2007 | Miyama et al. |
| 2008/0294140 A1* | 11/2008 | Ecker et al. ............ 604/385.23 |
| 2009/0312733 A1 | 12/2009 | Pellen et al. |
| 2011/0060301 A1 | 3/2011 | Nishikawa et al. |
| 2011/0251575 A1 | 10/2011 | Kuroda et al. |
| 2013/0267926 A1 | 10/2013 | Uematsu et al. |

FOREIGN PATENT DOCUMENTS

| | | |
|---|---|---|
| EP | 1493415 A2 | 1/2005 |
| EP | 1990033 A1 | 11/2008 |
| EP | 2248497 A1 | 11/2010 |
| EP | 2612635 A1 | 7/2013 |
| JP | 7-000449 A | 1/1995 |
| JP | 9-108262 A | 4/1997 |
| JP | 10-201788 A | 8/1998 |
| JP | 2002-272769 A | 9/2002 |
| JP | 2004-283231 A | 10/2004 |
| JP | 2006-510456 A | 3/2006 |
| JP | 2007-007456 A | 1/2007 |
| JP | 2009351 A | 1/2009 |
| JP | 2009-082480 A | 4/2009 |
| JP | 2010-148706 A | 7/2010 |
| JP | 201250699 A | 3/2012 |
| WO | 9005514 A1 | 5/1990 |
| WO | 2009110483 A1 | 9/2009 |

OTHER PUBLICATIONS

Office Action dated Dec. 30, 2013, corresponds to Chinese patent application No. 201010624516.5.

Office Action mailed Aug. 5, 2014, corresponding to Japanese patent application No. 2013-209421.

Office Action mailed Aug. 15, 2014, corresponding to Chinese patent application No. 201010624516.5.

International Search Report corresponding to PCT/JP2011/069604, dated Dec. 6, 2011.

Office Action dated Jan. 26, 2015, corresponding to Chinese patent application No. 201010624516.5.

Office Action mailed May 19, 2015, corresponding to Japanese patent application No. 2013-209421.

* cited by examiner

ABSORBENT ARTICLE WITH COMPRESSED GROOVES

RELATED APPLICATIONS

The present application is a National Phase of International Application Number PCT/JP2011/069604, filed Aug. 30, 2011, and claims priority from Japanese Application Number 2010-195861, filed Sep. 1, 2010.

TECHNICAL FIELD

The present invention relates to an absorbent article such as a sanitary napkin and a panty liner.

BACKGROUND ART

Conventionally, an elongated shaped absorbent article such as a sanitary napkin and a panty liner, provided with a top sheet having a skin contacting surface with which a wearer's skin is in contact, a back sheet that is disposed on an underwear side, and an absorbent core that is disposed between the top sheet and the back sheet, has been proposed. In such an absorbent article, a compressed groove is formed on the skin contacting surface to thereby reduce leakage of body fluid such as menstrual blood and urine from the skin contacting surface.

For example, Patent Document 1 proposes an absorbent article that reduces leakage from an end portion thereof in a longitudinal direction (rear portion) by arranging in tandem a plurality of substantially L-shaped compressed grooves extending in a width direction on a skin contacting surface of a rear portion, which is a first end side in a longitudinal direction.

Patent Document 1: Japanese Unexamined Patent Application Publication No. 2007-7456

DISCLOSURE OF THE INVENTION

Problems to be Solved by the Invention

However, in the absorbent article proposed in Patent Document 1, the body fluid flowing on the skin contacting surface toward the rear portion is guided to an outer side in the width direction along the substantially L-shaped compressed grooves, and the body fluid guided along the compressed grooves easily flows from both end portions of the compressed grooves toward outer sides in the width direction of the absorbent article. As a result, the absorbent article proposed in Patent Document 1 could not sufficiently reduce leakage of body fluid in the width direction from an end portion (rear portion) in the longitudinal direction.

Given this, the present invention is aimed at providing an absorbent article that can further reduce leakage of body fluid from an end portion in a longitudinal direction.

Means for Solving the Problems

The present invention relates to an elongated shaped absorbent article including: a liquid permeable top sheet that is disposed on a wearer's skin side and has a skin contacting surface; a liquid impermeable back sheet that is disposed on an underwear side; and a liquid absorptive absorbent core that is disposed between the top sheet and the back sheet, wherein: a compressed groove is formed on the skin contacting surface; the skin contacting surface has an excretory contact region that is positioned in a substantially central portion of the absorbent article in a longitudinal direction and in contact with the vicinity of the excretory part of the wearer, a front region that is positioned more on a front side than the excretory contact region, and a rear region that is positioned more on a rear side than the excretory contact region; the compressed groove has a pair of first central grooves that are arranged along the longitudinal direction of the absorbent article in the excretory contact region and a first circular groove that is provided in at least any one of the front region and the rear region; and the first circular groove is arranged at a position overlapping a vertical center line that extends in the longitudinal direction of the absorbent article.

In addition, it is preferable that the first circular groove is composed to have at least one bent point; and no more than one bent point is arranged at a position overlapping the vertical center line.

In addition, it is preferable that the first circular groove is disposed disproportionately to a first side in a width direction of the absorbent article; and the compressed groove further includes a second circular groove that is arranged to be spaced apart from the first circular groove toward a second side in the width direction of the absorbent article.

In addition, it is preferable that the first circular groove is arranged to be spaced apart from the pair of first central grooves.

In addition, it is preferable that a width of the first circular groove is smaller than a width of the pair of first central grooves.

In addition, it is preferable that the compressed groove further includes an outer groove that is arranged on an outer side of the first circular groove.

In addition, it is preferable that the outer groove is formed to be continued to the pair of first central grooves.

In addition, it is preferable that the compressed groove includes a low compression region that is formed by compressing the absorbent core with a predetermined pressure and a high compression region that is formed by compressing the absorbent core with a pressure greater than that used to form the low compression region.

Effects of the Invention

By the absorbent article according to the present invention, leakage of body fluid from the end portion in the longitudinal direction can further be reduced.

EXPLANATION OF REFERENCE NUMERALS

Figure 1:
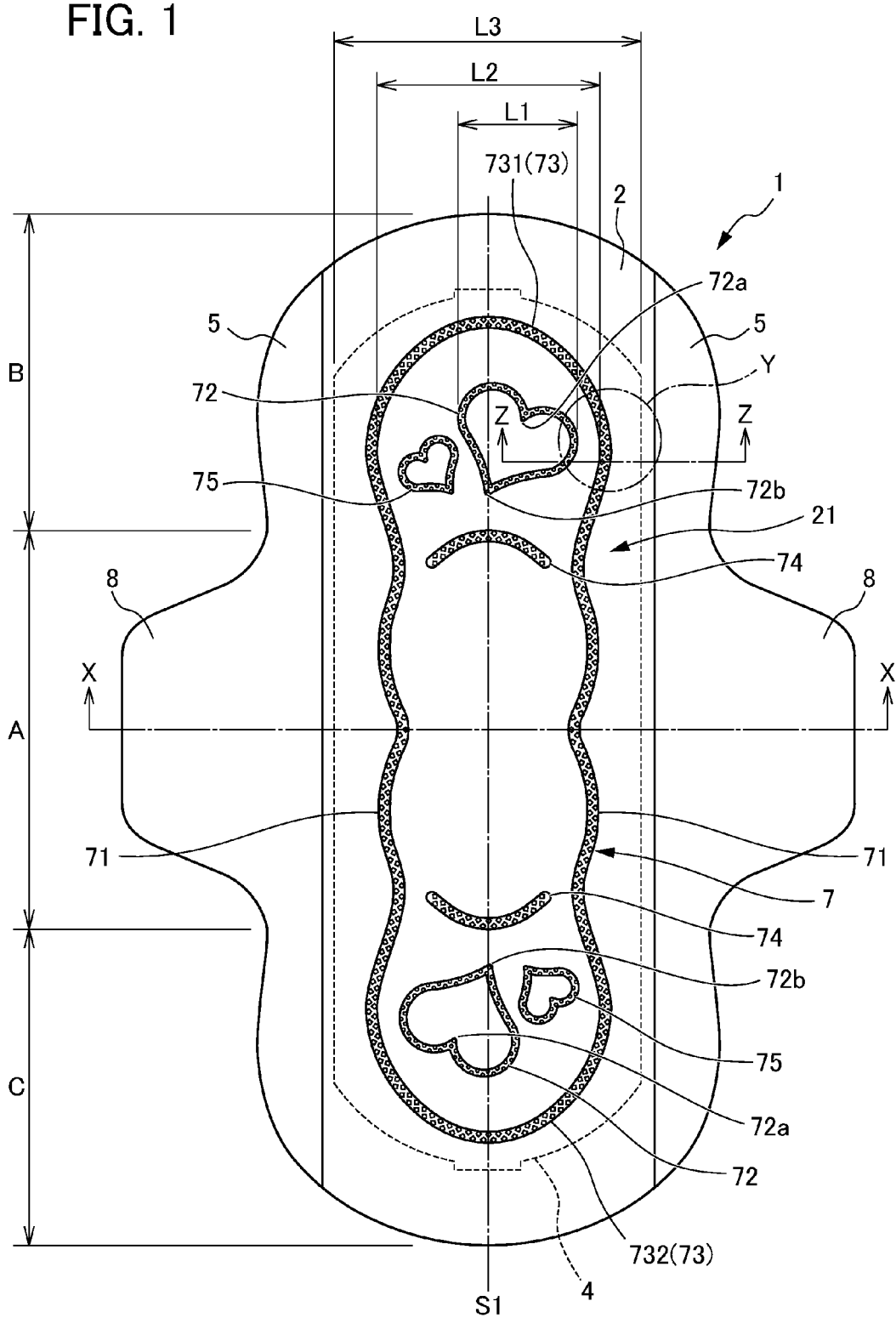
FIG. 1 is a plan view illustrating an absorbent article according to a first embodiment of the present invention.

1 Sanitary napkin (absorbent article)
4 Absorbent core

5 Side sheet
6 Second sheet
7 Compressed groove
8 Wing
71 First central groove
72 First designed groove (first circular groove)
73 Outer groove
74 Second central groove
75 Second designed groove (second circular groove)
A Excretory contact region
B Front region
C Rear region
S1 Vertical center line

PREFERRED MODE FOR CARRYING OUT THE INVENTION

Preferred embodiments of the absorbent article according to the present invention are explained hereinafter with reference to the drawings.

First, a sanitary napkin as the absorbent article according to the first embodiment of the present invention is described. FIG. 1 is a plan view illustrating a sanitary napkin 1 according to a first embodiment; and FIG. 2 is a cross-sectional view taken along the line X-X of FIG. 1.

Figure 2:
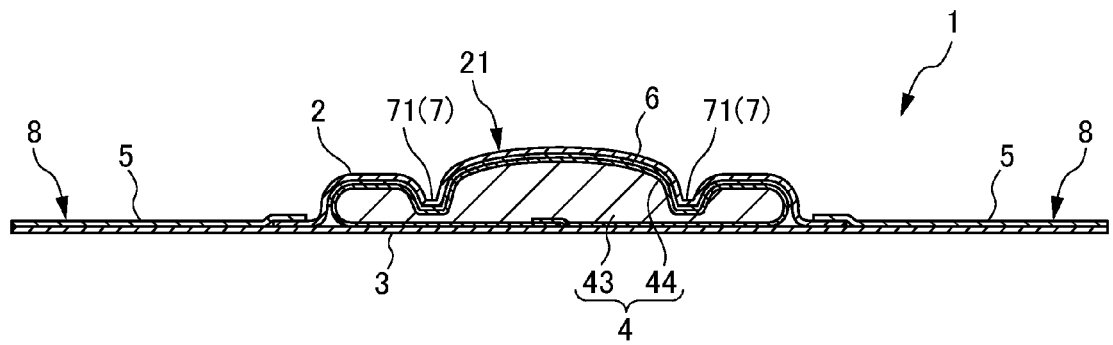
FIG. 2 is a cross-sectional view taken along the line X-X of FIG. 1.

As shown in FIGS. 1 and 2, the sanitary napkin 1 according to the first embodiment is configured in an elongated shape and to include a pair of wings 8 that projects outward in a width direction from a central portion in a longitudinal direction. As shown in FIGS. 1 and 2, the sanitary napkin 1 includes: a liquid permeable top sheet 2 that has a skin contacting surface 21 that is directed to a wearer's skin side and in contact with the wearer's skin during use;

a liquid impermeable back sheet 3 that is disposed on an underwear side;

a liquid absorptive absorbent core 4 that is disposed between the top sheet 2 and the back sheet 3;

a pair of side sheets 5 that is joined to a pair of side portions of the top sheet 2 and project outward from the pair of side portions; and a second sheet 6 (see FIG. 2) that is disposed between the top sheet 2 and the absorbent core 4.

The sanitary napkin 1 as shown in FIG. 1 has an excretory contact region A that is in contact with the vicinities of the excretory part of the wearer during use, a front region B that is positioned more on a wearer's belly side than the excretory contact region A during use, and a rear region C that is positioned more on a wearer's back side than the excretory contact region A during use.

More specifically, the excretory contact region A is a region in the sanitary napkin 1 in contact with a wearer's vaginal opening during use; for example, a region arranged between two leg openings of an underwear when the sanitary napkin 1 is used in a state of being attached to the underwear.

In the first embodiment, the excretory contact region A is a region corresponding to a region where wings 8 are arranged in the longitudinal direction of the sanitary napkin 1. The sanitary napkin 1 is triple-folded at folding lines (not illustrated) extending in the width direction in the vicinity of a borderline between the excretory contact region A and the front region B; and in the vicinity of a borderline between the excretory contact region A and the rear region C, and individually packaged in such a state. In other words, the excretory contact region A is a region that lies between the two folding lines.

As shown in FIG. 1, the top sheet 2 is formed in an elongated shape with a first end and a second end in the longitudinal direction having arcuate shapes. The top sheet 2 is configured to be greater in size than the absorbent core 4 in a planar view, and covers an entire region of an upper face of the absorbent core 4, as shown in FIG. 2.

The back sheet 3 is also configured to be greater in size than the absorbent core 4 and covers an entire region of a lower face of the absorbent core 4. The back sheet 3 projects outward from side edges of the absorbent core 4 at a position of the excretory contact region A in the width direction, thereby forming a part of the pair of wings 8.

The absorbent core 4 is configured in an elongated shape that is slightly smaller than the top sheet 2. The absorbent core 4 includes a liquid absorptive absorbent core main body 43 and a core wrapping material 44 that covers the absorbent core main body 43.

The second sheet 6 is liquid permeable and configured in a shape substantially the same as that of the absorbent core 4 in a planar view.

The pair of side sheets 5 is joined with the side portions of the back sheet 2 along the longitudinal direction. The pair of side sheets 5 projects outward at a position of the excretory contact region A in the width direction, thereby forming a part of the pair of wings 8. In other words, the pair of wings 8 is composed of the side sheet 5 and the back sheet 3 that are joined with each other.

The top sheet 2 and the back sheet 3 are joined with each other, in portions projecting from the front and rear ends of the absorbent core 4.

As the top sheet 2 and the second sheet 6, a perforated or non-perforated nonwoven fabric and a porous plastic sheet can be used. As the back sheet 3, for example, a hydrophobic nonwoven fabric, an impermeable plastic film, a laminate of nonwoven fabric and an impermeable plastic film, and the like can be used. Alternatively, as the back sheet 3, a melt-blown nonwoven fabric having high water-resisting property and a SMS nonwoven fabric sandwiched by high-strength spun-bonded nonwoven fabrics can be used.

As the absorbent core 4, for example, one obtained by wrapping the absorbent core main body 43 composed of: fluff pulp or an air-laid nonwoven fabric; and highly absorbent polymer, with the core wrapping material 44 such as tissue can be used.

As the fluff pulp used in the absorbent core main body 43, chemical pulp, cellulose fiber, and artificial cellulose fiber such as rayon, acetate, and the like can be exemplified. As the air-laid nonwoven fabric, one prepared by thermal fusion or binder fixation of a pulp with a synthetic fiber can be exemplified. As the highly absorbent polymer, granulous or fibrous polymer of starch, acrylic acid, and amino acid can be exemplified.

As the side sheet 5, a water repellent or hydrophobic sheet is preferably used. More specifically, various nonwoven fabrics such as spun lace nonwoven fabric, spun bond nonwoven fabric, thermal bond nonwoven fabric, melt-blown nonwoven fabric, needle-punched nonwoven fabric, air-through nonwoven fabric and the like can be used. As the fiber composing the nonwoven fabric, synthetic fiber of olefin such as polyethylene and polypropylene, polyester, polyamide and the like; regenerated fiber such as rayon and copra; and natural fiber such as cotton can be used.

As shown in FIGS. 1 and 2, on the skin contacting surface 21 of the sanitary napkin 1, a compressed groove 7 that is formed by integrally compressing the top sheet 2, the second sheet 6, and the absorbent core 4 is provided.

The compressed groove 7 includes: a pair of first central grooves 71; a first designed groove 72 as the first circular groove; an outer groove 73; a pair of second central grooves 74; and a second designed groove 75 as the second circular groove.

The pair of first central grooves 71 is arranged respectively on both side portions of the excretory contact region A and extends in the longitudinal direction of the sanitary napkin 1. More specifically, the pair of first central grooves 71 extends such that two curved parts that project outward in the width direction of the sanitary napkin 1 are arranged consecutively in the longitudinal direction. The pair of first central grooves 71 is arranged in line symmetrically with respect to a vertical center line S1 as a symmetrical axis extending in the longitudinal direction of the sanitary napkin 1.

The first designed groove 72 is an endless circular groove that is arranged in the front region B and in the rear region C. In the first embodiment, the first designed groove 72 is formed in a heart shape with two bent points: a bent point 72a projecting inward and a bent point 72b projecting outward. In the parts except for the two bent points, the first designed groove 72 consists of curved lines.

The first designed groove 72 is arranged such that the bent point 72b projecting outward (a lower end portion of the heart shape) is directed toward the excretory contact region A and that a part of the first designed groove 72 overlaps the vertical center line S1.

More specifically, the first designed groove 72 in the front region B is disposed disproportionately to a first side (right side in FIG. 1) in the width direction of the sanitary napkin 1. On the other hand, the first designed groove 72 in the rear region C is disposed disproportionately to a second side (left side in FIG. 2) in the width direction of the sanitary napkin 1. The first designed groove 72 is positioned such that the bent point 72b projecting outward overlaps the vertical center line S1 and that the bent point 72a projecting inward does not overlap the vertical center line S1. In other words, in the first designed groove 72, no more than one bent point is arranged at a position overlapping the vertical center line S1.

The outer groove 73 is arranged on the outside of the first designed groove 72. In the first embodiment, the outer groove 73 includes a front outer groove 731 arranged in the front region B and a rear outer groove 732 arranged in the rear region C.

The front outer groove 731 has a shape curved to project frontward, and a first end side and a second end side thereof are respectively connected to a front end side of the pair of first central grooves 71.

The rear outer groove 732 has a shape curved to project rearward, and a first end side and a second end side thereof are respectively connected to a rear end side of the pair of first central grooves 71.

The pair of second central grooves 74 is arranged in the vicinity of a borderline between the excretory contact region A and the front region B; and in the vicinity of a borderline between the excretory contact region A and the rear region C. The pair of second central grooves 74 extends in the width direction of the sanitary napkin 1 and is curved to project outward in the longitudinal direction of the sanitary napkin 1.

The second designed groove 75 is an endless circular groove that is arranged in the front region B and in the rear region C. In the first embodiment, the second designed groove 75 is formed in a heart shape smaller than the first designed groove 72. The second designed groove 75 is arranged away from the first designed groove 72, disproportionately to an opposite side to the first designed groove 72 in the width direction of the sanitary napkin 1. The second designed groove 75 is arranged not to overlap the vertical center line S1.

Figure 3:
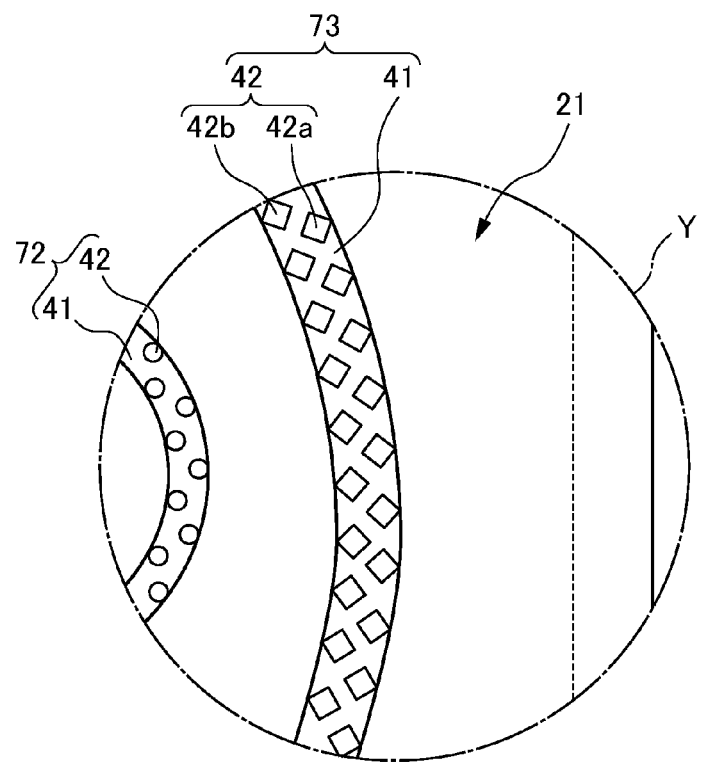
FIG. 3 is an enlarged view of a portion Y of FIG. 1.
Figure 4:
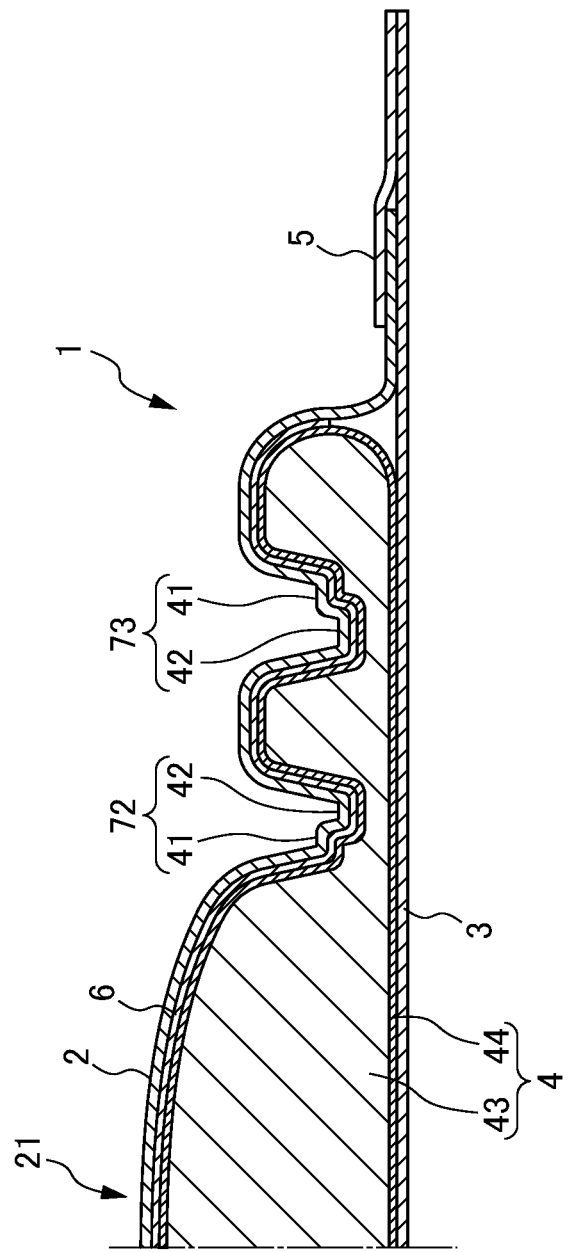
FIG. 4 is a cross-sectional view taken along the line Z-Z of FIG. 1.

FIG. 3 is a partially enlarged plan view of the sanitary napkin 1 according to the first embodiment, illustrating the compressed groove 7. FIG. 4 is a cross-sectional view taken along the line Z-Z of FIG. 1.

The compressed groove 7 is configured to include a low compression region 41 that is formed by compressing the absorbent core 4 with a predetermined pressure and a high compression region 42 that is formed by compressing the absorbent core 4 with a pressure greater than that used to form the low compression region 41. In addition, as shown in FIG. 1, the first designed groove 72 and the second designed groove 75 are configured to be smaller in width than the first central groove 71, the outer groove 73, and the second central groove 74.

In the first embodiment, in the first central groove 71, the outer groove 73 and the second central groove 74, a plurality of high compression regions 42 is formed at predetermined intervals within a low compression region 41, the high compressing regions 42 being in substantially square shapes in planar view. More specifically, the high compression region 42 includes: a plurality of outer high compression regions 42a that is arranged at predetermined intervals in a direction of the groove extending, thereby mainly constituting an outer side of the groove; and a plurality of inner high compression regions 42b that is arranged at predetermined intervals in the direction of the groove extending, thereby mainly constituting an inner side of the groove. The low compression region 41 is formed continuously in the direction of the groove extending.

Similar to the first central groove 71, the outer groove 73, and the second central groove 74, the first designed groove 72 and the second designed groove 75 are formed by providing a plurality of high compression regions 42 at predetermined intervals within the low compression region 41 that is formed continuously in the direction in which the groove extends. In the first designed groove 72 and the second designed groove 75, the high compression region 42 is in a substantially round shape in planar view, and is smaller than the outer high compression region 42a and the inner high compression region 42b. The first designed groove 72 and the second designed groove 75 are thus made smaller in width than the first central groove 71, the outer groove 73, and the second central groove 74.

In the compressed groove 7, the first designed groove 72 is arranged independently from the pair of first central grooves 71, the outer groove 73, the pair of second central grooves 74, and the second designed groove 75; in other words, arranged away from the pair of first central grooves 71, the outer groove 73, the pair of second central grooves 74, and the second designed groove 75. In addition, the pair of second central grooves 74 is arranged independently from the pair of first central grooves 71, the first designed groove 72, the outer groove 73, and the second designed groove 75. On the inside of the pair of first central grooves 71 and the pair of second central grooves 74 in the excretory contact region A, no compressed groove is formed.

In the first embodiment, from the viewpoint of effectively preventing leakage of body fluid from end portions in the longitudinal direction of the sanitary napkin 1, a length L1 (see FIG. 1) in the width direction of the first designed groove 72 (an end-to-end length of the groove) is preferably 25 to 90% and more preferably 50 to 90% of a length L2 in the width direction of a region surrounded by the outer groove 73 (an inner length of the groove).

In a case in which the outer groove 73 is not provided, from the viewpoint of effectively preventing leakage of body fluid from end portions in the longitudinal direction of the sanitary napkin 1, a proportion of the length L1 (see FIG. 1) in the width direction of the first designed groove 72 with respect to a length L3 (see FIG. 1) of the absorbent core 4 in the width direction is preferably 25 to 100%, and more preferably 50 to 100%.

The sanitary napkin 1 according to the first embodiment is manufactured as follows, for example.

First, fluff pulp and highly absorbent polymer are layered to form the absorbent core main body 43; and the absorbent core main body 43 is wrapped with the core wrapping material 44 to form the absorbent core 4.

And then, a continuous body of the second sheet 6 is placed on an upper surface of a continuous body of the top sheet 2 being conveyed; the absorbent core 4 is placed on an upper surface of the continuous body of the second sheet 6; and continuous body of the top sheet 2, the continuous body of the second sheet 6, and the absorbent core 4 are joined with each other by a hotmelt adhesive.

Thereafter, the continuous body of the top sheet 2, to which the continuous body of the second sheet 6 and the absorbent core 4 are joined, is passed between a pair of compressing rollers with projections of a predetermined shape formed on a circumference thereof (not illustrated), to thereby form the compressed groove 7 being depressed from a side of the continuous body of the top sheet 2.

Next, a joint body of the absorbent core 4 and the continuous body of the top sheet 2 with the compressed groove 7 is reversed, and a continuous body of the back sheet 3 and a continuous body of the side sheet 5 (not illustrated) are joined to the joint body of the absorbent core 4 and the continuous body of the top sheet 2 thus reversed, to thereby form a continuous body of the sanitary napkin 1.

Finally, the continuous body of the sanitary napkin 1 is cut in a predetermined size and shape by a cutter, to thereby obtain the sanitary napkin 1.

The above-described sanitary napkin 1 according to the first embodiment produces the following effects.

(1) The pair of central grooves 71 is provided in the excretory contact region A on the skin contacting surface 21 and the circular first designed groove 72 is provided respectively in the front region B and the rear region C. As a result, the body fluid that is discharged from the excretory part of a wearer and then flows on the skin contacting surface 21 from the excretory contact region A toward the front region B and the rear region C is drawn to the first designed groove 72, which is compressed to be high in density, and then quickly migrates to the absorbent core 4. In addition, since the first designed groove 72 is configured to be endless, the body fluid thus drawn in cannot migrate easily to the outside of the first designed groove 72. Leakage of body fluid from the end portions in the longitudinal direction can thus be further reduced.

In addition, since the first designed groove 72 is arranged at a position overlapping the vertical center line S1, even if a force in the width direction of the sanitary napkin 1 is applied from wearer's thighs and buttocks, excessive deformation of the sanitary napkin 1 in the width direction at folding lines extending in the longitudinal direction can be prevented. Given this, flexibility is maintained in the excretory contact region A to follow the wearer's body motion while the excessive deformation of the sanitary napkin 1 in the width direction is prevented in the front region B and the rear region C, thereby preventing reduction in absorptive area of the sanitary napkin 1 due to twisting.

(2) The first designed groove 72 is arranged away from the first central groove 71, the outer groove 73, the second central groove 74 and the second designed groove 75. This can prevent the body fluid that is drawn into the circular first designed groove 72 from being drawn to other grooves. As a result, the effect of preventing leakage of body fluid by the first designed groove 72 can be improved.

(3) The front outer groove 731 and the rear outer groove 732 are provided on the outside of the first designed groove 72. Leakage of body fluid from the skin contacting surface 21 can thus be further reduced.

(4) The front outer groove 731 and the rear outer groove 732 are formed to connect respectively to the pair of first central groove 71. Leakage of body fluid from the skin contacting surface 21 can thus be further reduced.

(5) The pair of second central grooves 74 is provided in the vicinity of a borderline between the excretory contact region A and the front region B; and in the vicinity of a borderline between the excretory contact region A and the rear region C. Migration of body fluid from the excretory contact region A to the front region B and the rear region C can thus be reduced by the pair of second central groove 74, thereby further improving a leakage prevention effect of the sanitary napkin 1.

(6) In the first designed groove 72, the number of the bent point that overlaps the vertical center line S1 is no greater than one. As a result, since no more than one bent point is present at the position overlapping the vertical center line S1, even if a force in the width direction of the sanitary napkin 1 is applied from wearer's thighs and buttocks, excessive deformation of the sanitary napkin 1 at folding lines generated between bent points in the front region B and the rear region C can be prevented. Twisting of the sanitary napkin 1 can further be prevented, to thereby further prevent reduction in the body fluid absorptive area of the sanitary napkin 1 due to twisting.

(7) The first designed groove 72 is arranged disproportionately to a first side in the width direction of the sanitary napkin 1, while the second designed groove 75 is arranged on a second side in the width direction of the sanitary napkin 1. This can increase a proportion of the length in the width direction of an area in which the first designed groove 72 and the second designed groove 75 are provided to the entire length in the width direction of the sanitary napkin 1. An effect of preventing leakage of body fluid from the end portions in the longitudinal direction of the sanitary napkin 1 can thus be further improved.

(8) An area of each of the high compression regions 42 in the first designed groove 72 and the second designed groove 75 is configured to be smaller than an area of each of the high compression regions 42 in the first central groove 71, the outer groove 73 and the second central groove 74; and a width of the first designed groove 72 and the second designed groove 75 is configured to be smaller than a width of the first central groove 71, the outer groove 73 and the second central groove 74. The first designed groove 72 and the second designed groove 75 are thus made more flexible than the first central groove 71, the outer groove 73, and the second central groove 74, thereby reducing an uncomfortable sensation felt by the wearer.

(9) The first designed groove 72 in the front region B is arranged disproportionately to a first side in the width direction of the sanitary napkin 1, while the first designed groove 72 in the rear region C is arranged disproportionately to a second side in the width direction of the sanitary napkin 1. This can increase a proportion of the length in the width direction of an area in which the first designed groove 72 is provided to the entire length in the width direction of the sanitary napkin 1, to thereby increase stiffness against a force applied to the sanitary napkin 1 from the width direction. As a result, an excessive deformation of the sanitary napkin 1 in the width direction can further be prevented.

(10) The sanitary napkin 1 is configured such that, on the inside of the pair of first central grooves 71 and the pair of second central grooves 74 in the excretory contact region A, no compressed groove is formed. As a result, since a following capability of the sanitary napkin 1 to the wearer's body motion is not impaired in a region between the pair of first central grooves 71 and a region between the pair of second central grooves 74, an effect of preventing leakage of body fluid by the sanitary napkin 1 can further be improved.

(11) The first designed groove 72 and the second designed groove 75 are configured in heart shapes. This can improve appearance of the skin contacting surface 21 of the sanitary napkin 1 and can provide visual prettiness to the sanitary napkin 1, thereby alleviating the wearer's unpleasant feeling during the menstrual period.

Figure 5:
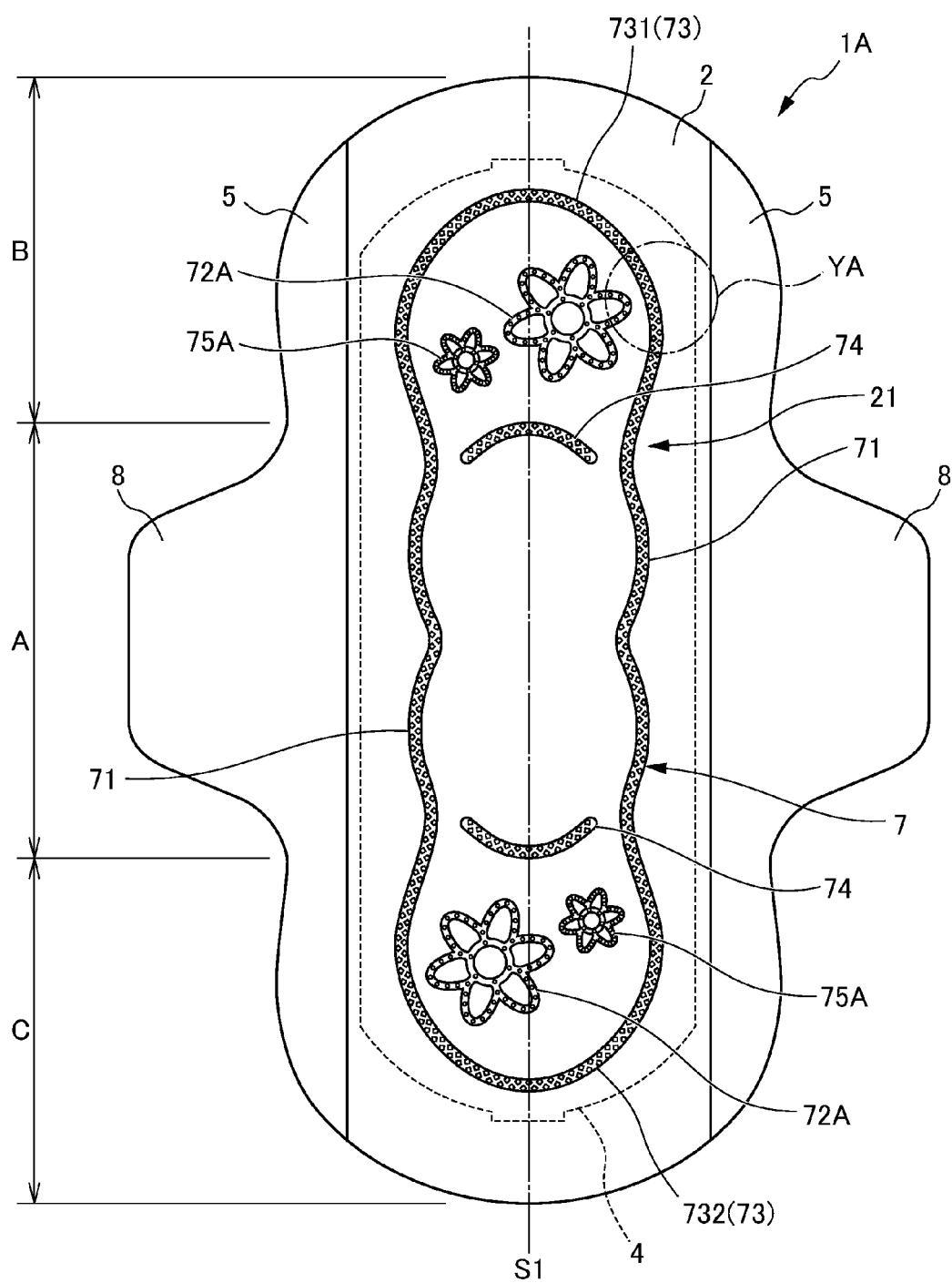
FIG. 5 is a plan view illustrating an absorbent article according to a second embodiment of the present invention.
Figure 6:
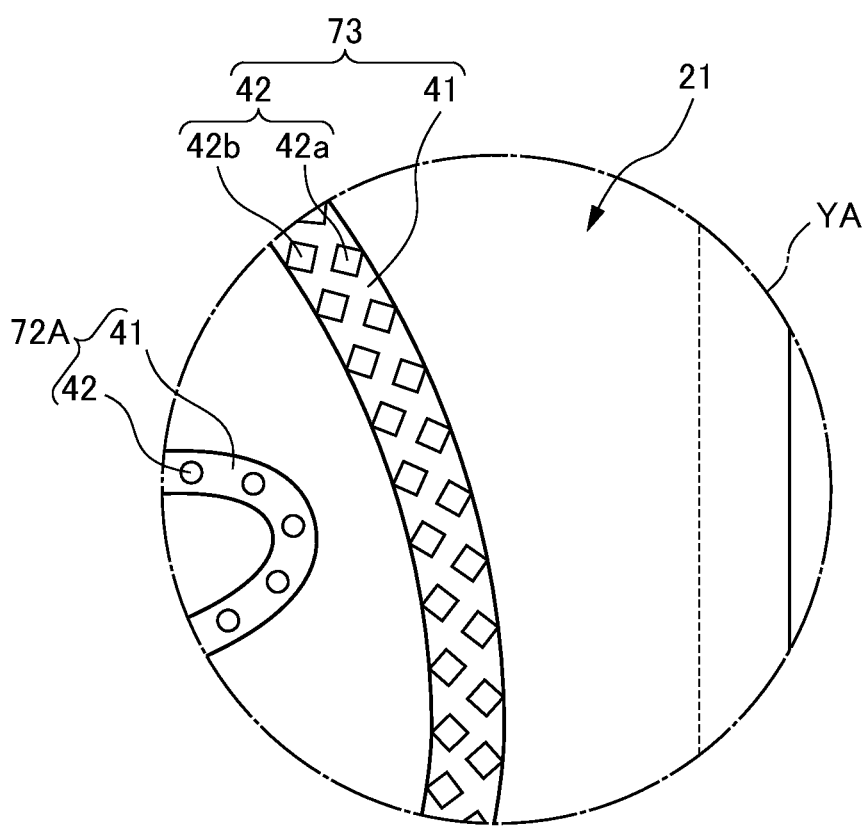
FIG. 6 is an enlarged plan view of a portion YA of FIG. 5.

Next, a second embodiment of the sanitary napkin of the present invention is described hereinafter with reference to FIGS. 5 and 6. FIG. 5 is a plan view illustrating the sanitary napkin 1A according to the second embodiment; and FIG. 6 is a partially enlarged plan view of FIG. 5. In the following description of the second embodiment, the same components are denoted by the same reference numerals, and description thereof will be omitted or simplified.

The sanitary napkin 1A according to the second embodiment is different from the first embodiment mainly in the shapes of the first designed groove 72A and the second designed groove 75A.

More specifically, in the second embodiment, the first designed groove 72A and the second designed groove 75A are configured in flower shapes. In other words, the first designed groove 72A and the second designed groove 75A are configured in flower shapes by arranging a plurality of oval shaped grooves radially around a periphery of round shaped grooves.

In addition, in the second embodiment, in the first designed groove 72A and the second designed groove 75A, the high compression regions are formed in a line along the direction in which the groove extends. The high compression region 42 is in a substantially round shape in planar view, and is smaller than the outer high compression region 42a and the inner high compression region 42b. The first designed groove 72A and the second designed groove 75A are thus made smaller in width than the first central groove 71, the outer groove 73, and the second central groove 74.

The second embodiment produces the following effects, in addition to the abovementioned effects (1) to (10).

(11) The first designed groove 72A and the second designed groove 75A are configured in flower shapes. This can improve appearance of the skin contacting surface 21 of the sanitary napkin 1A and can provide visual prettiness to the sanitary napkin 1A, thereby alleviating the wearer's unpleasant feeling during the menstrual period.

Figure 7:
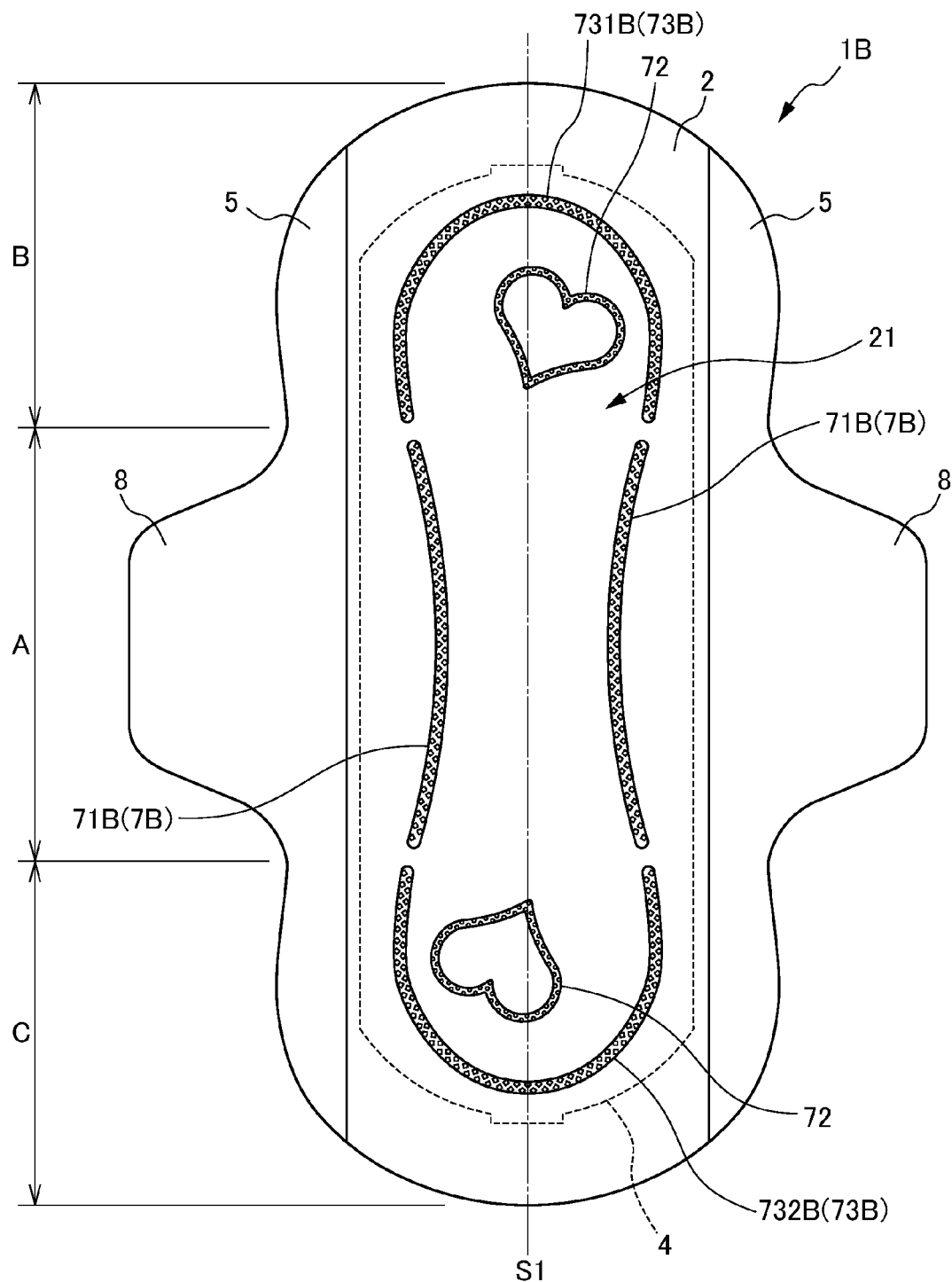
FIG. 7 is a plan view illustrating an absorbent article according to a third embodiment of the present invention.

Next, a third embodiment of the sanitary napkin of the present invention is described hereinafter with reference to FIG. 7. FIG. 7 is a plan view illustrating the sanitary napkin 1B according to the third embodiment.

The sanitary napkin 1B of the third embodiment is different from the first embodiment mainly: in that the second central groove and the second designed groove are not provided; and in the arrangement of the outer groove 73B.

More specifically, in the third embodiment, the pair of first central grooves 71B extends to be curved to project inward in the width direction of the sanitary napkin 1.

In addition, in the third embodiment, the first end and the second end of the front outer groove 731B are arranged away from the front end of the pair of first central grooves 71B, as shown in FIG. 7. Furthermore, the first end and the second end of the rear outer groove 732B are arranged away from the rear end of the pair of first central grooves 71B.

The third embodiment provides the abovementioned effects (1) to (3), (6), and (8) to (11).

The preferred embodiments of the absorbent article according to the present invention have been described above; however, the present invention is not limited thereto and can be embodied in various modes.

For example, in the first to third embodiments, the sanitary napkin 1 is configured to include the pair of second central grooves 74; however, the present invention is not limited thereto. In other words, the sanitary napkin can be configured without the pair of second central grooves.

Furthermore, in the first embodiment and the second embodiment, the first designed groove and the second designed groove are formed in the same shape; however, the present invention is not limited thereto. In other words, the first designed groove and the second designed groove can be formed in different shapes.

Moreover, in the first to third embodiments, the present invention is employed in sanitary napkins; however, the present invention is not limited thereto. In other words, the present invention can also be employed in other absorbent articles, such as panty liners and incontinence pads.

In addition, in the first to third embodiments, the entire first designed groove is arranged in the front region B or the rear region C; however, the present invention is not limited thereto. In other words, the first designed groove can be arranged such that a part of the first designed groove (for example, no more than 20% of the length in the longitudinal direction of the first designed groove) is positioned at the excretory contact region A.

Furthermore, for example, both of the sanitary napkin 1 of the first embodiment with the first designed groove 72 in the heart shape and the sanitary napkin 1A of the second embodiment with the first designed groove 72A in the flower shape can be packaged in a single package. The sanitary napkin thus packaged can provide a user with fun of guessing the shape of the first designed groove.

The invention claimed is:

1. An elongated absorbent article, comprising:
   a liquid permeable top sheet that is disposed on a wearer's skin side and has a skin contacting surface;
   a liquid impermeable back sheet that is disposed on an underwear side; and
   a liquid absorptive absorbent core that is disposed between the top sheet and the back sheet,
   wherein
   a compressed groove is formed in the absorbent core and on the skin contacting surface,
   the skin contacting surface has
      an excretory contact region that is positioned in a substantially central portion of the absorbent article in a longitudinal direction of the absorbent article and is configured to be in contact with a vicinity of the excretory part of the wearer, a front region that is positioned in front of the excretory contact region, and a rear region that is positioned in rear of the excretory contact region, the compressed groove has a pair of first central grooves arranged along the longitudinal direction of the absorbent article respectively on two side portions of the excretory contact region, wherein the first central grooves are symmetrical with respect to each other across a vertical center line which is a symmetrical axis extending in the longitudinal direction of the absorbent article, a pair of second central grooves spaced apart from the first central grooves, wherein one of the second central grooves is arranged in a vicinity of a borderline between the excretory contact region and the front region, and the other of the second central grooves is arranged in a vicinity of a borderline between the excretory contact region and the rear region, a pair of first grooves, one of the first grooves being provided in the front region and the other of the first grooves being provided in the rear region, a pair of second grooves, one of the second grooves being provided in the front region and the other of the second grooves being provided in the rear region, and a pair of outer grooves, one of the outer grooves being provided in the front region and the other one of the outer grooves being provided in the rear region, in each of the front region and the rear region, the outer groove is arranged on an outer side of the first groove and the second groove, and spaced apart from the first groove and the second groove, the first groove is spaced apart from both the pair of first central grooves and the pair of second central grooves, the second groove is spaced apart from both the pair of first central grooves and the pair of second central grooves, the first groove is formed in a heart shape disposed disproportionately to a first side in the width direction with respect to the vertical center line, and has a first bent point projecting inward of the heart shape and a second bent point projecting outward of the heart shape, the second bent point is arranged at a position overlapping the vertical center line, the first bent point is arranged at a position which does not overlap the vertical center line, the second groove is disposed disproportionately to a second side in the width direction with respect to the vertical center line, a pattern of the second groove is smaller than the heart shape of the first groove and does not overlap the vertical center line, the second side opposite the first side in the width direction, and the first groove is spaced apart from the second groove, the first grooves and the second grooves are smaller in width than the first central grooves, the outer grooves, and the second central grooves, the compressed groove includes low compression regions where the absorbent core is compressed with a first predetermined pressure, and high compression regions where the absorbent core is compressed with a second predetermined pressure greater than the first predetermined pressure, and an area of each of the high compression regions in the first grooves and the second grooves is smaller than an area of each of the high compression regions in the first central grooves, the outer grooves and the second central grooves.

2. The absorbent article according to claim 1, wherein each of the outer grooves is continuous to the pair of first central grooves.

3. The absorbent article according to claim 1, wherein in each of the front region and the rear region, the second groove is formed in a heart shape smaller than the heart shape of the first groove.

4. The absorbent article according to claim 1, wherein, in the compressed groove, a pattern of each of the high compression regions in the first grooves and the second grooves is different from a pattern of each of the high compression regions in the first central grooves, the outer grooves and the second central grooves.

5. The absorbent article according to claim 2, wherein a greatest dimension of the heart shape of the first groove in the width direction is 25 to 90% of a greatest dimension of a region surrounded by the outer groove in the width direction.

6. The absorbent article according to claim 2, wherein a greatest dimension of the heart shape of the first groove in the width direction is 50 to 90% of a greatest dimension of a region surrounded by the outer groove in the width direction.

7. An elongated shaped absorbent article, comprising:

a liquid permeable top sheet that is disposed on a wearer's skin side and has a skin contacting surface;

a liquid impermeable back sheet that is disposed on an underwear side; and a liquid absorptive absorbent core that is disposed between the top sheet and the back sheet, wherein a compressed groove is formed in the absorbent core and on the skin contacting surface;

the skin contacting surface has an excretory contact region that is positioned in a substantially central portion of the absorbent article in a longitudinal direction of the absorbent article and is configured to be in contact with a vicinity of the excretory part of the wearer, a front region that is positioned in front of the excretory contact region, and a rear region that is positioned in rear of the excretory contact region;

the compressed groove has a pair of first central grooves arranged along the longitudinal direction of the absorbent article respectively on two side portions of the excretory contact region, wherein the first central grooves are symmetrical with respect to each other across a vertical center line which is a symmetrical axis extending in the longitudinal direction of the absorbent article, a pair of first grooves, one of the first grooves being provided in the front region and the other of the first grooves being provided in the rear region, and a pair of outer grooves, one of the outer grooves being provided in the front region and the other of the outer grooves being provided in the rear region, in each of the front region and the rear region, the outer groove is on an outer side of the first groove, and spaced apart from the first groove, the first groove is spaced apart from the pair of first central grooves, the first groove is formed in a heart shape disposed disproportionately to a first side in the width direction with respect to the vertical center line, and has a first bent point projecting inward of the heart shape and a second bent point projecting outward of the heart shape, the second bent point is arranged at a position overlapping the vertical center line, the first bent point is arranged at a position which does not overlap the vertical center line, the first grooves are smaller in width than the first central grooves and the outer grooves, wherein the compressed groove includes low compression regions where the absorbent core is compressed with a first predetermined pressure, and high compression regions where the absorbent core is compressed with a second predetermined pressure greater than the first predetermined pressure, and wherein an area of each of the high compression regions in the first grooves is smaller than an area of each of the high compression regions in the first central grooves and the outer grooves.

8. The absorbent article according to claim 7, the compressed groove further includes:

a pair of second central grooves spaced apart from the first central grooves, wherein one of the second central grooves is arranged in the vicinity of a borderline between the excretory contact region and the front region, and the other of the second central grooves is arranged in a vicinity of a borderline between the excretory contact region and the rear region, and a pair of second grooves, one of the second grooves being provided in the front region and the other of the second grooves being provided in the rear region, wherein each of the outer grooves is continuous to the pair of first central grooves, in each of the front region and the rear region, the second groove is spaced apart from both the pair of first central grooves and the pair of second central grooves, the second groove is disposed disproportionately to a second side in the width direction with respect to the vertical center line, a pattern of the second groove is smaller than the heart shape of the first groove and does not overlap the vertical center line, the second side opposite the first side in the width direction, and an area of each of the high compression regions in the second grooves is smaller than an area of each of the high compression regions in the first central grooves, the outer grooves and the second central grooves.

9. The absorbent article according to claim 8, wherein in each of the front region and the rear region, the second groove is formed in a heart shape smaller than the heart shape of the first groove.

10. The absorbent article according to claim 9, wherein in each of the compressed grooves, a pattern of each of the high compression regions in the first grooves and the second grooves is different from a pattern of each of the high compression regions in the first central grooves, the outer grooves and the second central grooves.

* * * * *